US012582560B2

(12) United States Patent
Perttunen

(10) Patent No.: US 12,582,560 B2
(45) Date of Patent: Mar. 24, 2026

(54) CANINE DIAPER ASSEMBLY

(71) Applicant: Jordan Perttunen, Chanhassen, MN (US)

(72) Inventor: Jordan Perttunen, Chanhassen, MN (US)

( * ) Notice: Subject to any disclaimer, the term of this patent is extended or adjusted under 35 U.S.C. 154(b) by 360 days.

(21) Appl. No.: 18/201,161

(22) Filed: May 23, 2023

(65) Prior Publication Data

US 2024/0390193 A1     Nov. 28, 2024

(51) Int. Cl.
*A61F 13/42* (2006.01)
*A61F 13/15* (2006.01)

(52) U.S. Cl.
CPC .... *A61F 13/42* (2013.01); *A61F 2013/15186* (2013.01); *A61F 2013/422* (2013.01)

(58) Field of Classification Search
CPC ........................ A61F 2013/15186; A61F 13/42
See application file for complete search history.

(56) References Cited

U.S. PATENT DOCUMENTS

| | | |
|---|---|---|
| 7,602,302 B2 | 10/2009 | Hokuf |
| 8,314,284 B1 | 11/2012 | Novello |
| 9,633,540 B1 | 4/2017 | Teshome |
| 2005/0139168 A1 | 6/2005 | Light |
| 2014/0090608 A1* | 4/2014 | Komatsubara ......... A01K 23/00 |
| | | 119/869 |
| 2014/0203797 A1 | 7/2014 | Stivoric |
| 2019/0060136 A1* | 2/2019 | Turner ................. A01K 13/006 |
| 2019/0083326 A1* | 3/2019 | Komatsubara ......... A01K 23/00 |
| 2019/0357499 A1* | 11/2019 | Komatsubara ........ A61F 13/514 |

FOREIGN PATENT DOCUMENTS

WO     WO2016191770     12/2016

* cited by examiner

*Primary Examiner* — Catharine L Anderson
*Assistant Examiner* — Meagan Ngo

(57) ABSTRACT

A canine diaper assembly includes a band that is wearable around a canine's body. The band is constructed of a fluid impermeable material to inhibit urine of the canine from passing through the band. A first tab is coupled to and extends away from the band and a second tab is coupled to and extends away from the band. The second tab is matable to the first tab for retaining the band in a closed loop around the canine's body. An absorbent pad is integrated into the band to absorb urine from the canine. A reactive strip is integrated into the band and the reactive strip is comprised of a material which chemically reacts to urine. The reactive strip changes colors when the reactive strip is exposed to urine to visually communicate that the canine has urinated into the absorbent pad.

7 Claims, 7 Drawing Sheets

CANINE DIAPER ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to diaper devices and more particularly pertains to a new diaper device for absorbing urine from a canine. The device includes a fluid impermeable band that can be wrapped around the canine's torso and an absorbent pad integrated into the band for absorbing urine from the canine. The device includes a reactive strip that is integrated into the band which reacts to the presence of urine. Furthermore, the reactive strip changes color when the reactive strip is exposed to urine to visually communicate that the canine has urinated.

(2) Description of Related Art Including Information Disclosed Under 37 CFR 1.97 and 1.98

The prior art relates to diaper devices including a tracking apparatus that is wearable on a canine and which is in wireless communication with a personal electronic device. The prior art discloses a diaper change alert device that includes an oblong sensor and a speaker integrated into the oblong sensor. The oblong sensor is positionable in a diaper and the speaker is turned on when the oblong sensor is exposed to urine. The prior art discloses a defecation control system that includes an ingestible tracker and a monitor that is wearable on a host that receives an alert signal when the ingestible tracker is defecated.

BRIEF SUMMARY OF THE INVENTION

An embodiment of the disclosure meets the needs presented above by generally comprising a band that is wearable around a canine's body. The band is comprised of a fluid impermeable material to inhibit urine of the canine from passing through the band. A first tab is coupled to and extends away from the band and a second tab is coupled to and extends away from the band. The second tab is matable to the first tab for retaining the band in a closed loop around the canine's body. An absorbent pad is integrated into the band to absorb urine from the canine. A reactive strip is integrated into the band and the reactive strip is comprised of a material which chemically reacts to urine. Furthermore, the reactive strip changes colors when the reactive strip is exposed to urine to visually communicate that the canine has urinated into the absorbent pad.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
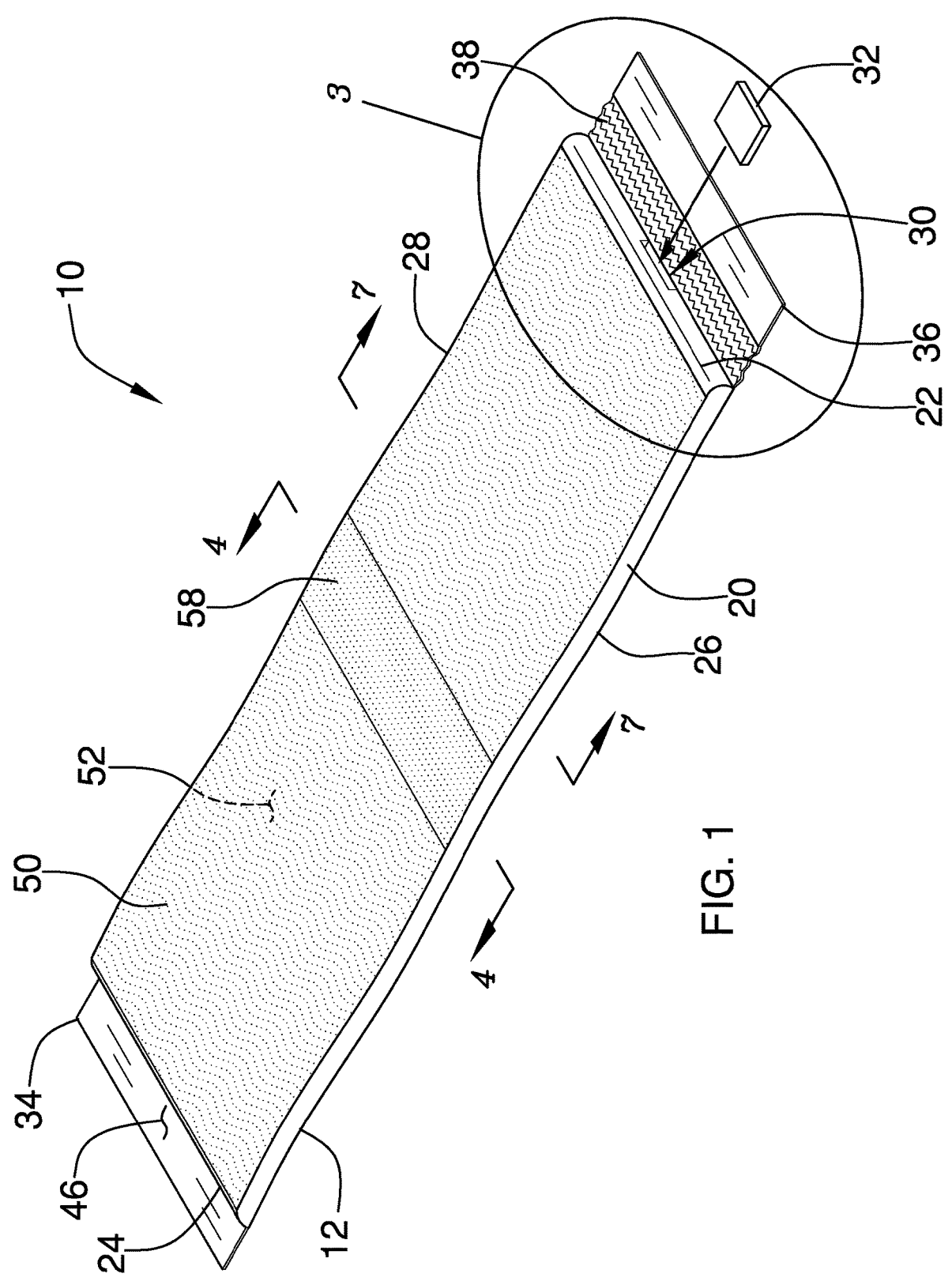
FIG. 1 is a top perspective view of a canine diaper assembly according to an embodiment of the disclosure.
Figure 2:
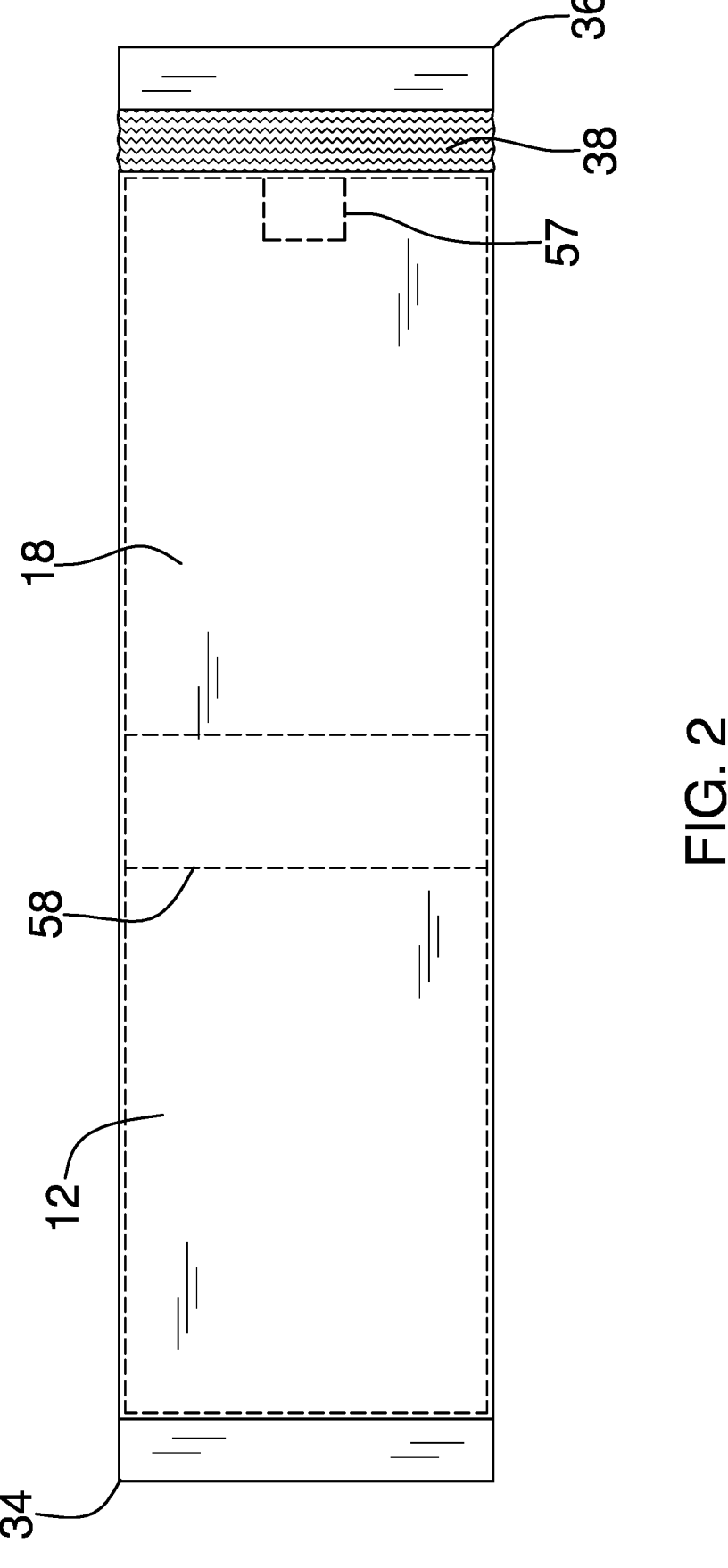
FIG. 2 is a bottom phantom view of an embodiment of the disclosure.
Figures 3, 4:
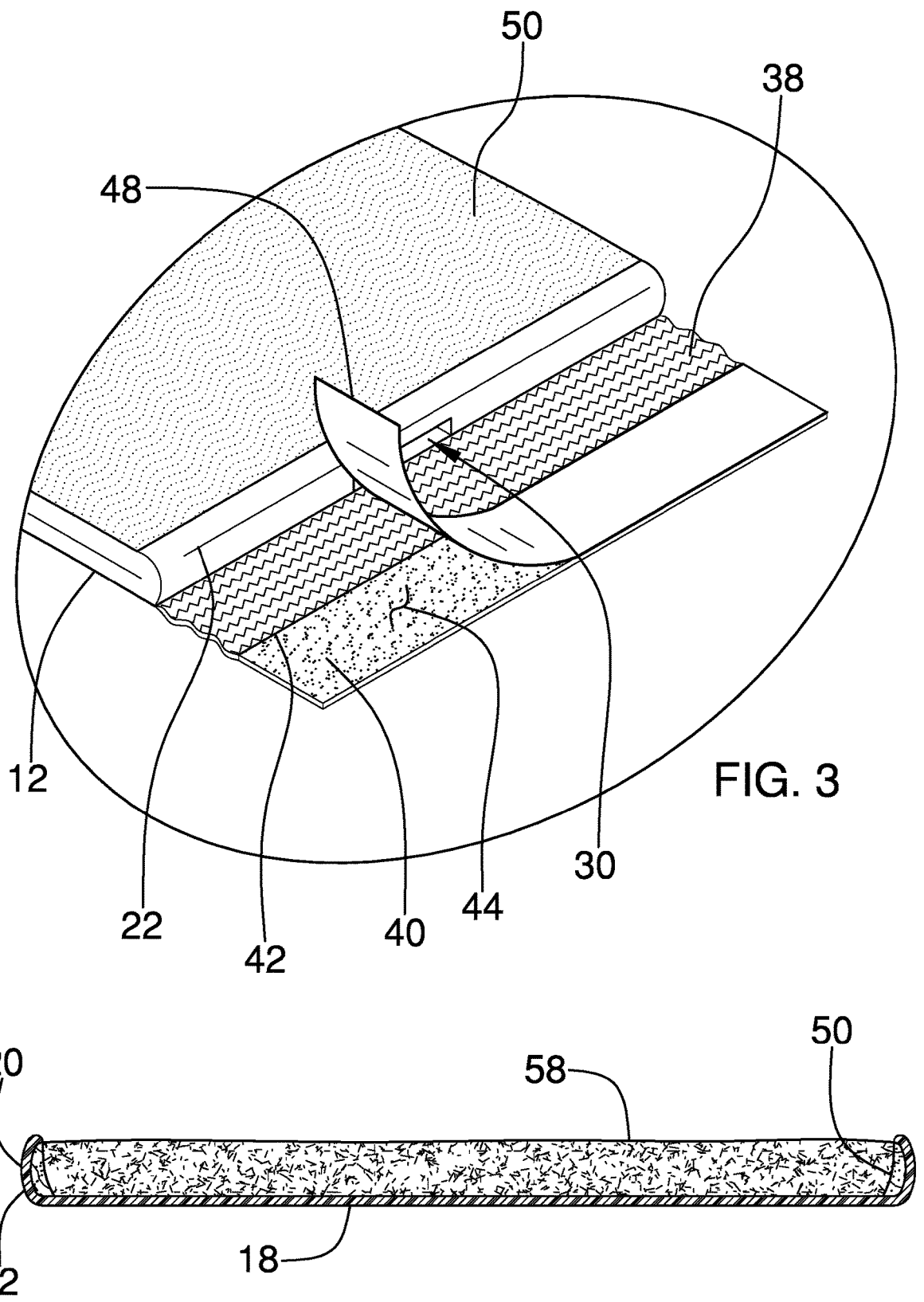
FIG. 3 is a front perspective view taken from circle 3 of FIG. 1 of an embodiment of the disclosure.
FIG. 4 is a cross sectional view taken along line 4-4 of FIG. 1 of an embodiment of the disclosure.
Figure 5:
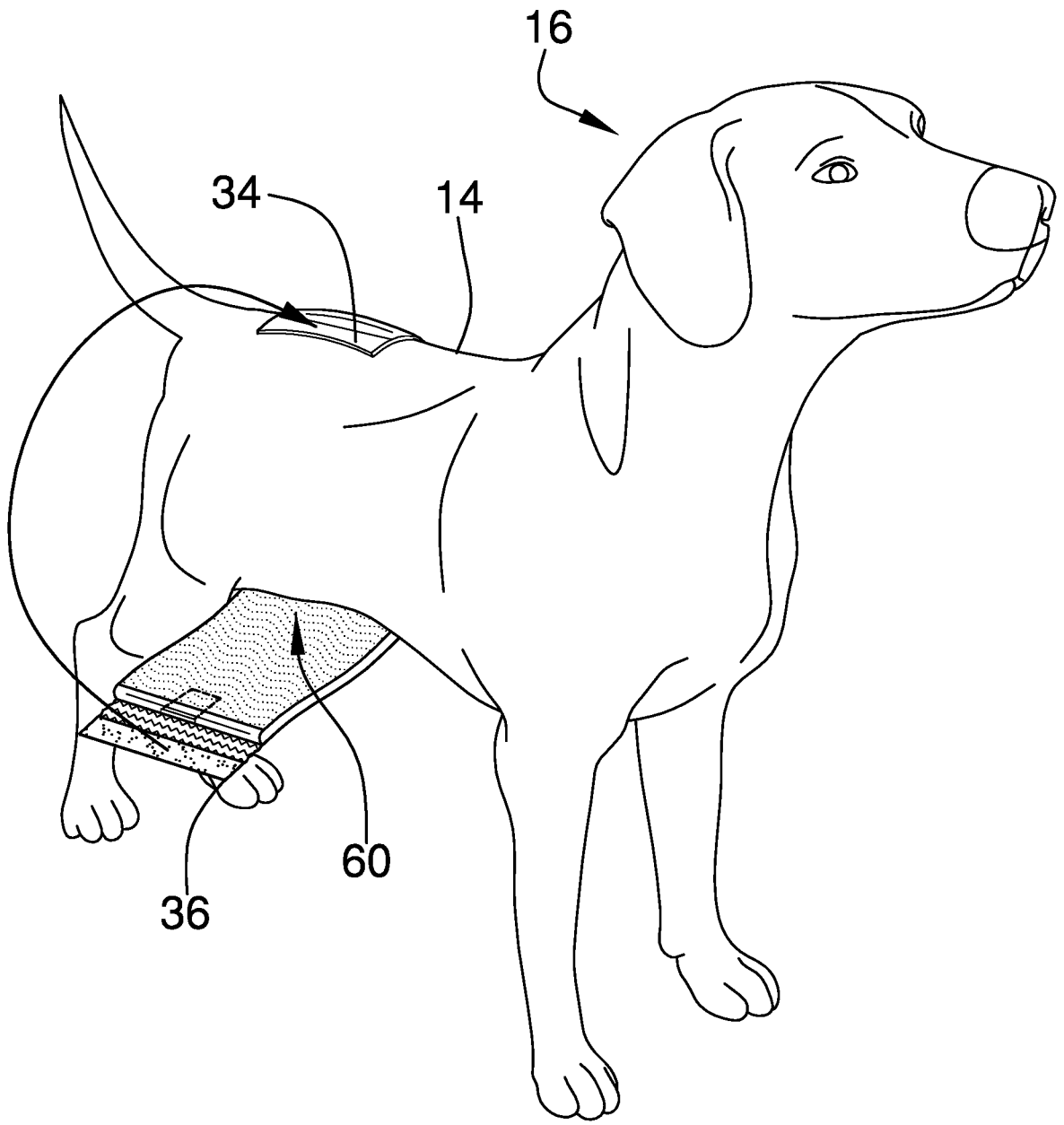
FIG. 5 is a perspective in-use view of an embodiment of the disclosure showing a band being wrapped around a canine's torso.
Figure 6:
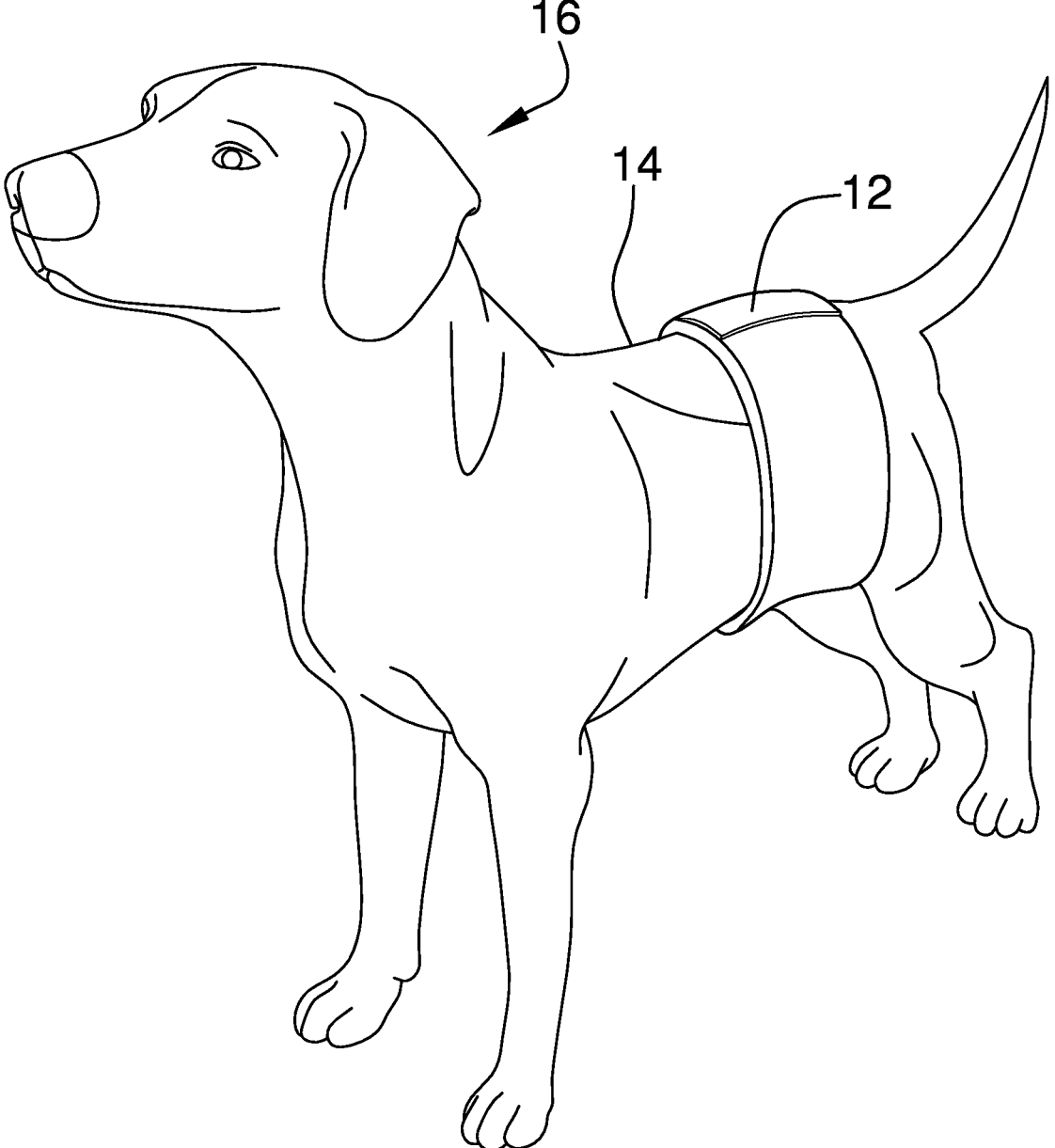
FIG. 6 is a perspective in-use view of an embodiment of the disclosure showing a band being worn around a canine's torso.
Figure 7:
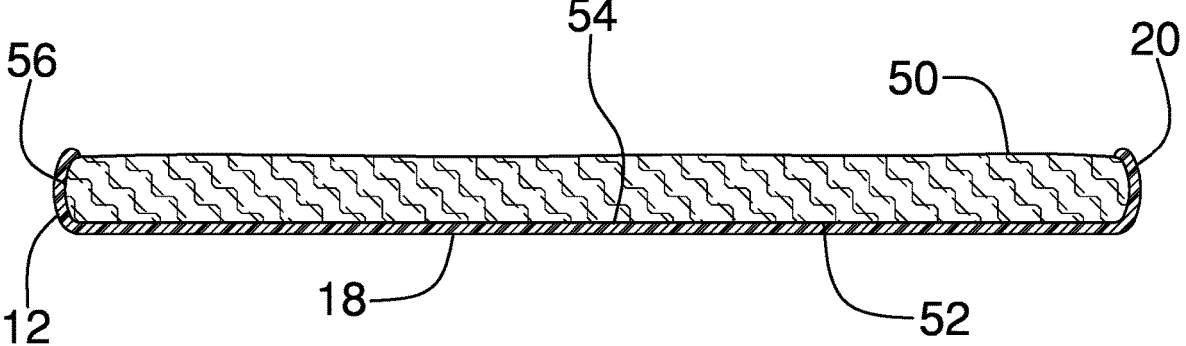
FIG. 7 is a cross sectional view taken along line 7-7 of FIG. 1 of an embodiment of the disclosure.

With reference now to the drawings, and in particular to FIGS. 1 through 8 thereof, a new diaper device embodying the principles and concepts of an embodiment of the disclosure and generally designated by the reference numeral 10 will be described.

As best illustrated in FIGS. 1 through 8, the canine diaper assembly 10 generally comprises a band 12 that is wearable around a torso 14 of a canine 16. The band 12 is comprised of a fluid impermeable material to inhibit urine of the canine 16 from passing through the band 12. The band 12 has a basal wall 18 and a perimeter wall 20 extending upwardly from the basal wall 18 and the perimeter wall 20 has a front side 22, a back side 24, a first lateral side 26 and a second lateral side 28. Each of the front side 22 and the back side 24 curves toward a center of the basal wall 18 and the front side 22 has an opening 30 extending through the front side 22. A global positioning chip 32 can be inserted into the opening 30 thereby facilitating the canine 16 to be tracked by a personal electronic device, for example, or other type of electronic device that has wireless communication capabilities.

A first tab 34 is coupled to and extends away from the band 12 and the first tab 34 is disposed on the back side 24 of the perimeter wall 20 of the band 12. Additionally, the first tab 34 extends along a full width of the back side 24 of the perimeter wall 20. A second tab 36 is coupled to and extends away from the band 12 and the second tab 36 is matable to the first tab 34 for retaining the band 12 in a closed loop around the canine's torso 14. The second tab 36 comprises an elastomeric band 38 that is coupled to and extends away from the front side 22 of the perimeter wall 20 of the band 12. The elastomeric band 38 extends along a full width of the front side 22 of the perimeter wall 20.

The second tab 36 includes an adhesive pad 40 that is coupled to and extends away from a distal edge 42 of the elastomeric band 38. The adhesive pad 40 has an upwardly facing surface 44 which adhesively engages an exposed surface 46 of the first tab 34. A protective sheet 48 is removably bonded to the upwardly facing surface 44 for inhibiting the upwardly facing surface 44 from adhering to an object. Furthermore, the protective sheet 48 completely covers the upwardly facing surface 44.

An absorbent pad 50 is integrated into the band 12 thereby facilitating the absorbent pad 50 to abut the canine's torso 14 when the band 12 is wrapped around the canine's torso 14. The absorbent pad 50 is comprised of a fluid absorbent material to absorb urine from the canine 16. The absorbent pad 50 has a lower surface 52 that is bonded to a top surface 54 of the basal wall 18 of the band 12 and an outer edge 56 that is surrounded by the perimeter wall 20 of the band 12. In this way the perimeter wall 20 inhibits urine from leaking outwardly from the absorbent pad 50. The absorbent pad 50 has a well 57 extending into the outer edge 56 which is aligned with the opening 30 in the front side 22 of the perimeter wall 20 of the band 12 for storing the global positioning chip 32.

A reactive strip 58 is integrated into the band 12 and the reactive strip 58 is comprised of a material which chemically reacts to urine thereby. Furthermore, the reactive strip 58 changes colors when the reactive strip 58 is exposed to urine. In this way the reactive strip 58 can visually communicate that the canine 16 has urinated into the absorbent pad 50. The reactive strip 58 extends between the first lateral side 26 and the second lateral side 28 of the perimeter wall 20 of the band 12 and the reactive strip 58 is centrally positioned between the front side 22 and the back side 24 of the perimeter wall 20. As is most clearly shown in FIG. 4, the reactive strip 58 bisects the absorbent pad 50 and the band 12 may be comprised of a translucent material thereby facilitating the reactive strip 58 to be visible through the basal wall 18 of the band 12. Thus, the reactive strip 58 to be visible when the band 12 is worn around the canine's torso 14. Furthermore, the color displayed by the reactive strip 58 when the reactive strip 58 is exposed to urine may be green, red or other color that contrasts with the appearance of the band 12.

Figure 8:
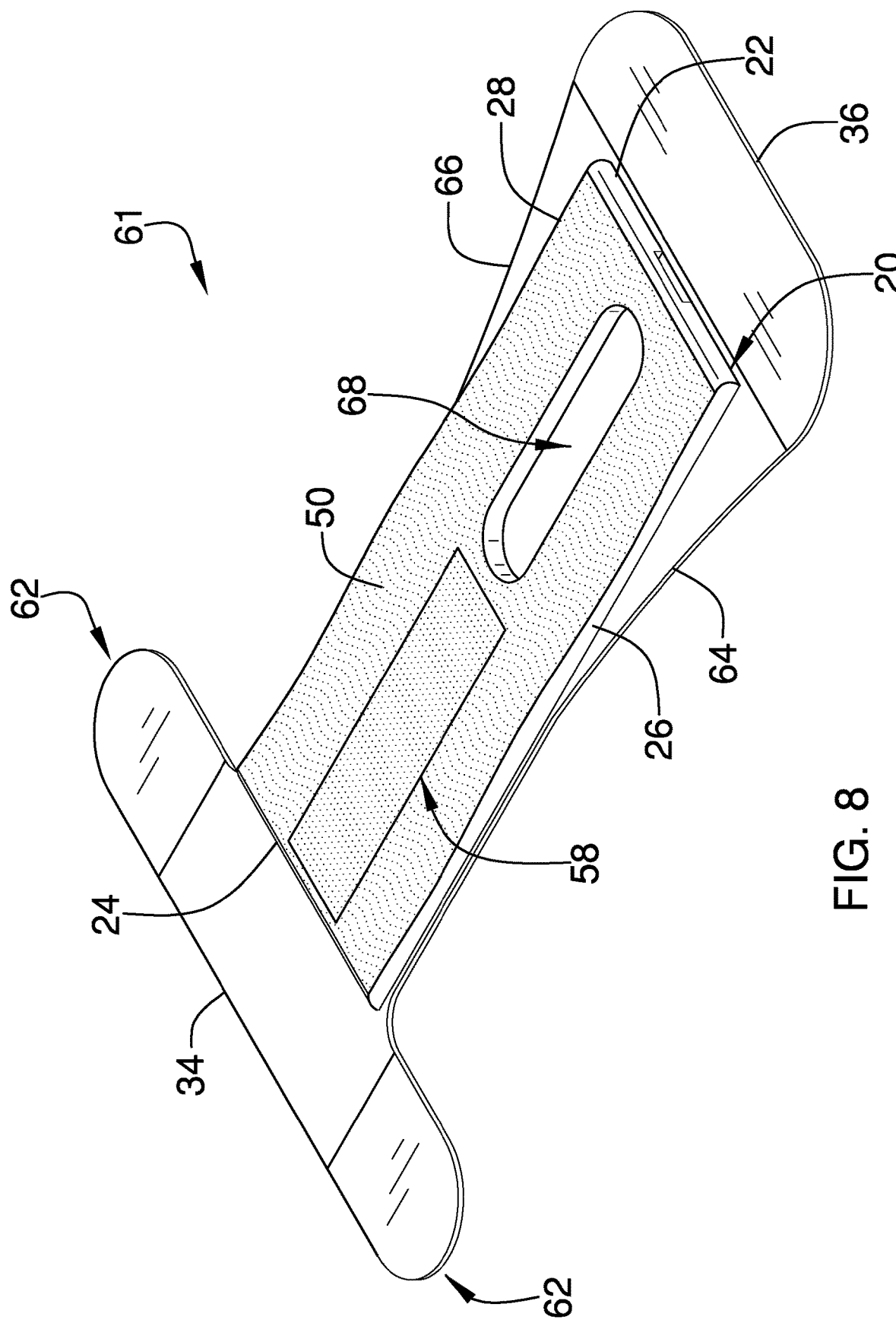
FIG. 8 is a perspective in-use of an alternative embodiment of the disclosure.

In an alternative embodiment 61 shown in FIG. 8, the first tab 34 extends laterally beyond each of the first lateral side 26 and the second lateral side 28 of the perimeter wall 20 of the band 12 to define a pair of lobes 62 on the first lateral side 26 and the second lateral side 28. The second tab 36 has a first lateral edge 64 and a second lateral edge 66 that each curves front the perimeter wall 20 of the band adjacent to the front side 22 of the perimeter wall 20 such that the second tab 36 has a width that is greater than a width of the front side 22. The band 12 has a tail hole 68 which extends through the basal wall 18 to accommodate a tail 70 of a female canine 16. The tail hole 68 is elongated along an axis extending between the front side 22 and the back side 24 of the perimeter wall 20 and the tail hole 68 is positioned closer to the front side 22 than the back side 24. The tail hole 68 extends through the absorbent pad 50 thereby facilitating the absorbent pad 50 to absorb urine from the female canine 16. The reactive strip 58 is elongated to extend along the axis extending between the front side 22 and the back side 24 and the reactive strip 58 is positioned between the tail hole 68 and the first tab 34.

In use, the protective sheet 48 is removed from the adhesive pad 40, the band 12 is wrapped around the canine's torso 14 and the adhesive pad 40 is adhered to the first tab 34. Furthermore, the band 12 is aligned with the canine's genitalia 60 thereby facilitating the absorbent pad 50 to absorb urine when the canine 16 urinates. In this way the canine 16 is inhibited from urinating on a floor of a house, for example, when the canine 16 is indoors. Furthermore, the perimeter wall 20 of the band 12 inhibits the urine from leaking out of the absorbent pad 50. The reactive strip 58 changes color when the reactive strip 58 is exposed to urine thereby visually communicating that the band 12 should be removed from the canine 16 and discarded.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A canine diaper assembly for absorbing urine from a canine, said assembly comprising:

a band being wearable around a canine's body, said band being comprised of a fluid impermeable material wherein said band is configured to inhibit urine of the canine from passing through said band;

a first tab being coupled to and extending away from said band;

a second tab being coupled to and extending away from said band, said second tab being matable to said first tab for retaining said band in a closed loop around the canine's body;

an absorbent pad being integrated into said band thereby facilitating said absorbent pad to abut the canine's body when said band is wrapped around the canine's body, said absorbent pad being comprised of a fluid absorbent material wherein said absorbent pad is configured to absorb urine from the canine;

a reactive strip being integrated into said band, said reactive strip being comprised of a material which chemically reacts to urine thereby facilitating said reactive strip to change colors when said reactive strip is exposed to urine wherein said reactive strip is configured to visually communicate that the canine has urinated into said absorbent pad;

wherein said band has a basal wall and a perimeter wall extending upwardly from said basal wall, said perimeter wall having a front side, a back side, a first lateral side and a second lateral side, each of said front side and said back side curving toward a center of said basal wall, said front side having an opening extending through said front side;

wherein said first tab is disposed on said back side of said perimeter wall of said band; and wherein said second tab comprises an elastomeric band being coupled to and extending away from said front side of said perimeter wall of said band.

2. The assembly according to claim 1, wherein said second tab includes:

an adhesive pad being coupled to and extending away from a distal edge of said elastomeric band, said adhesive pad having an upwardly facing surface which adhesively engages an exposed surface of said first tab; and a protective sheet being removably bonded to said upwardly facing surface for inhibiting said upwardly facing surface from adhering to an object, said protective sheet completely covering said upwardly facing surface.

3. The assembly according to claim 1, wherein said absorbent pad has a lower surface being bonded to a top surface of said basal wall of said band, said absorbent pad having an outer edge being surrounded by said perimeter wall of said band wherein said perimeter wall is configured to inhibit urine from leaking outwardly from said absorbent pad.

4. The assembly according to claim 1, wherein said reactive strip extends between said first lateral side and said second lateral side of said perimeter wall of said band, said reactive strip being centrally positioned between said front side and said back side of said perimeter wall, said reactive strip being visible through said basal wall of said band thereby facilitating said reactive strip to be visible when said band is worn around the canine's body.

5. A canine diaper assembly for absorbing urine from a canine, said assembly comprising:

a band being wearable around a canine's body, said band being comprised of a fluid impermeable material wherein said band is configured to inhibit urine of the canine from passing through said band, said band having a basal wall and a perimeter wall extending upwardly from said basal wall, said perimeter wall having a front side, a back side, a first lateral side and a second lateral side, each of said front side and said back side curving toward a center of said basal wall, said front side having an opening extending through said front side;

a first tab being coupled to and extending away from said band, said first tab being disposed on said back side of said perimeter wall of said band;

a second tab being coupled to and extending away from said band, said second tab being matable to said first tab for retaining said band in a closed loop around the canine's body, said second tab comprising:

an elastomeric band being coupled to and extending away from said front side of said perimeter wall of said band;

an adhesive pad being coupled to and extending away from a distal edge of said elastomeric band, said adhesive pad having an upwardly facing surface which adhesively engages an exposed surface of said first tab; and a protective sheet being removably bonded to said upwardly facing surface for inhibiting said upwardly facing surface from adhering to an object, said protective sheet completely covering said upwardly facing surface;

an absorbent pad being integrated into said band thereby facilitating said absorbent pad to abut the canine's body when said band is wrapped around the canine's body, said absorbent pad being comprised of a fluid absorbent material wherein said absorbent pad is configured to absorb urine from the canine, said absorbent pad having a lower surface being bonded to a top surface of said basal wall of said band, said absorbent pad having an outer edge being surrounded by said perimeter wall of said band wherein said perimeter wall is configured to inhibit urine from leaking outwardly from said absorbent pad; and a reactive strip being integrated into said band, said reactive strip being comprised of a material which chemically reacts to urine thereby facilitating said reactive strip to change colors when said reactive strip is exposed to urine wherein said reactive strip is configured to visually communicate that the canine has urinated into said absorbent pad, said reactive strip extending between said first lateral side and said second lateral side of said perimeter wall of said band, said reactive strip being centrally positioned between said front side and said back side of said perimeter wall, said reactive strip being visible through said basal wall of said band thereby facilitating said reactive strip to be visible when said band is worn around the canine's body.

6. The assembly according to claim 5, wherein:

said first tab extends laterally beyond each of said first lateral side and said second lateral side of said perimeter wall of said band to define a pair of lobes on said first lateral side and said second lateral side;

each of said first lateral side and said second lateral side curves outwardly adjacent to said front side of said perimeter wall such that said second tab has a width being greater than a width of said front side; and said band has a tail hole extending through said basal wall wherein said tail hole is configured to accommodate a tail of a female canine, said tail hole being elongated along an axis extending between said front side and said back side of said perimeter wall, said tail hole being positioned closer to said front side than said back side, said tail hole extending through said absorbent pad.

7. The assembly according to claim 6, wherein said reactive strip is elongated to extend along said axis extending between said front side and said back side, said reactive strip being positioned between said tail hole and said first tab.

* * * * *